United States Patent
Asakage et al.

Patent Number: 5,494,950
Date of Patent: Feb. 27, 1996

[54] EPOXY RESIN COMPOSITION CONTAINING ALKYLATED HYDROQUINONE EPOXIDE

[75] Inventors: Hideyasu Asakage, Tokyo; Michio Aritomi, Chiba; Xiao Li Wu, Tsuchiura, all of Japan

[73] Assignee: Totokasei Co., Ltd., Tokyo, Japan

[21] Appl. No.: 223,680

[22] Filed: Apr. 6, 1994

[30] Foreign Application Priority Data

Apr. 16, 1993 [JP] Japan .................. 5-126469

[51] Int. Cl.⁶ .................................. C08L 63/00
[52] U.S. Cl. .................... 523/427; 523/428; 523/443; 523/466; 525/481; 525/482; 525/484; 528/102; 528/103; 549/560
[58] Field of Search .................. 525/481, 482, 525/484; 523/443, 466, 427, 428; 528/102, 103

[56] References Cited

U.S. PATENT DOCUMENTS

| | | | |
|---|---|---|---|
| 4,876,324 | 10/1989 | Nakano et al. | 528/144 |
| 4,900,801 | 2/1990 | Takata et al. | 549/560 |
| 5,360,837 | 11/1994 | Honda et al. | 523/220 |

OTHER PUBLICATIONS

Chemical Abstracts 114:34416, "Printed Circuit Boards Containing Epoxy Resin Compositions", Tominaga et al.
Chemical Abstracts 113:98814, "Low Dielectric Epoxy Resin Compositions Containing Polystyrene", Tominaga et al.
Chemical Abstracts: 71(13) 60943k.
Chemical Abstracts: 67(3) 11288j.
Chemical Abstracts: 117(22) 213828x.
Chemical Abstracts: 113(20) 173472k.
Chemical Abstracts: 104(26) 234346k.
Chemical Abstracts: 83(22) 180167e.
Chemical Abstracts: 80(22) 122584r.
Chemical Abstracts: 70(16) 69336b.
Chemical Abstracts: 74(14) 64985k.
Chemical Abstracts: 75(3) 19950e.
Chemical Abstracts: 70(10) 38401g.
Chemical Abstracts: 67(17) 82131p.
Chemical Abstracts: 71(14) 62170e.

*Primary Examiner*—Frederick Krass
*Attorney, Agent, or Firm*—Sherman and Shalloway

[57] ABSTRACT

An epoxy resin composition comprising an epoxy resin component containing at least 5% by weight of an epoxy resin of Formula [I], an epoxy hardener, and an inorganic filler as essential constituents:

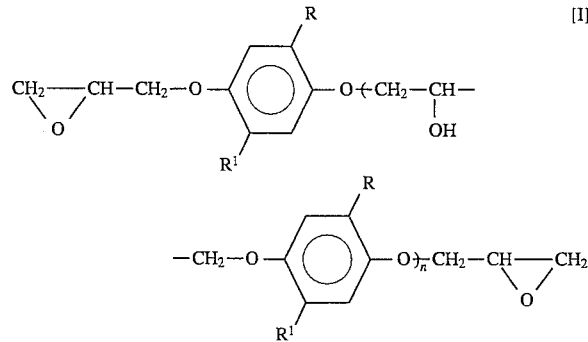

[wherein R and $R^1$ denote alkyl of $C_2$ to $C_6$, and n is an integer repetition unit from 0 to 10.]. The epoxy resin composition, when used as a molding material, is low in water absorption rate and flexural modulus (low stress).

4 Claims, No Drawings

EPOXY RESIN COMPOSITION CONTAINING ALKYLATED HYDROQUINONE EPOXIDE

FIELD OF THE INVENTION

This invention relates to an epoxy resin composition which is suited for use in the electric and electronic industry, especially for use as an IC encapsulating material, more specifically, to an epoxy resin composition comprising an epoxy resin of a derivative containing specific structures in 2- and 5-positions of hydroquinone, an epoxy hardener, and an inorganic filler, and molding of the composition can be endowed with low stress and water absorption and high heat resistance.

DESCRIPTION OF PRIOR ART

Epoxy resin is used in a substrate for constructing electronic devices and parts such as LSIs and laminate boards and, recently, is drawing attention as an IC sealing material in the field of electronics which is under a rapid technical innovation.

In general, an epoxy resin composition used in these epoxy resin molding compounds produced from an epoxy resin, a hardener, an accelerator, a filler, a fire retardant agent, a coupling agent, a gelease agent, and a coloring agent, which are mixed and kneaded to form a composition and used as a molding compound.

Heretofore, as a epoxy resin for these molding compounds, an o-cresol novolac type epoxy resin is widely used for its heat resistance, moldability, and electrical characteristics. However, recently, with the tendency of semiconductor devices to higher integration, compact and thin-walled packages, and improved packaging efficiency, the epoxy resin composition for use in these applications is required to have even higher heat resistance and even lower water absorption and stress.

To improve the stress characteristics of the epoxy resin composition, it is effective to increase the content of inorganic fillers such as a filler mainly comprising fused silica to reduce the thermal expansion coefficient of the composition and, since such inorganic fillers are superior in heat resistance and low water absorption, they are effective to meet requirements for heat resistance and low water absorption and stress.

However, there has been a problem in that the use of o-cresol novolac type epoxy resin, which has been widely used in the past, and increased amounts of inorganic fillers tend to result in an increase in melt viscosity and a considerable decrease in fluidity during molding, damaging fine-structured electronic devices to be sealed. Therefore, it is preferable to use an epoxy resin which has a low viscosity in the vicinity of the molding temperature.

Low-viscosity epoxy resins include bisphenol A type epoxy resin, which is liquid at room temperature, and bisphenol F type epoxy resin, which is even lower in viscosity, and are used to good advantage in liquid sealing. However, when used in a low-pressure transfer molding method, they require considerable renovation or installation of new equipment or lead to a deterioration in workability, which is disadvantageous in economy and industrial application.

From this point of view, an epoxy resin having a crystallinity is drawing industrial attention. The crystalline epoxy resin, which is solid at room temperature, can be handled in existing equipment and, when the melting point of crystal is exceeded, exhibits a rapid increase in fluidity, and can deal with the problems of moldability and damages to fine electronic devices even though the amounts of inorganic fillers are increased.

As such a crystalline epoxy resin, there is known one which is based on hydroquinone obtained by reacting hydroquinone with epichlorohydrin. This resin has a crystal melting point, of 90° to 110° C. and a sufficiently low viscosity at the molding temperature (150°–180° C.), but the resin itself has a high water absorption rate, and its composition tends to be less reliable.

There is also known a crystalline epoxy resin which is obtained by dihydroxybiphenyls with epichlorohydrin, but, the viscosity tends to increase in the vicinity of the molding temperature, and its composition filled with large amounts of inorganic fillers is dissatisfactory in terms of fluidity.

Further, an epoxy resin obtained by condensation reaction of β-naphthol and formaldehyde is also crystalline, but has an insufficient melt viscosity and is thus difficult to use.

OBJECT OF THE INVENTION

A primary object of the present invention is to provide an epoxy resin composition having improved water absorption, stress, and heat resistance, which could not be attained by the prior art technology.

SUMMARY OF THE INVENTION

The inventors have conducted insensitive studies to obtain an epoxy resin composition having a low water absorption rate, a low stress, and a high heat resistance and accomplished the present invention. In accordance with the present invention, there is provided: (1) an epoxy resin composition comprising an epoxy resin component containing at least 5% by weight of an epoxy resin of Formula [I], an epoxy hardener, and an inorganic filler:

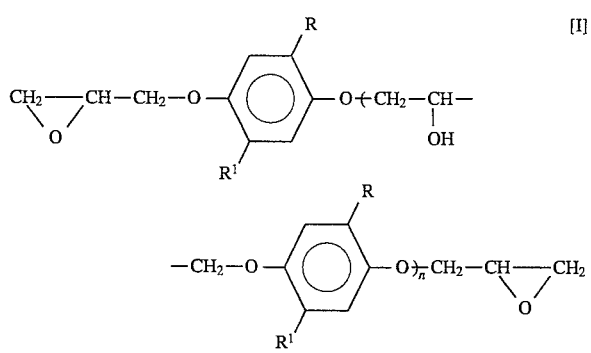

[wherein R and $R^1$ denote alkyl of $C_2$ to $C_6$, and n is an integer repetition unit from 0 to 10.].

There is also provided according to the present invention: (2) an epoxy resin composition of claim 1 wherein the epoxy resin of Formula [I] is crystalline and has a crystal melting point of 50° C. to 150° C.

There is further provided according to the present invention: (3) an epoxy resin composition of claim 1 wherein the epoxy resin of Formula [I] has a melt viscosity of 0.1 poise or less at 150° C.

Practical examples of the epoxy resin of Formula [I] include, but are not limited to, 2,5-di-tert-butylhydroquinonediglycidylether, 2,5-di-sec-butyl-hydroquinonediglycidylether, 2,5-diethylhydroquinonediglycidylether, 2,5-tert-amylhydroquinonediglycidylether, and the like.

The epoxy resin of Formula [I] is that of a derivative having alkyl of $C_2$ to $C_6$ at 2- and 5-positions of hydroquinone, which is crystalline at room temperature, has a crystal melting point of 50° C. to 150° C., and has a melt viscosity of 0.1 poise or less at 150° C.

An epoxy resin of a compound having a mono-alkyl substituent on hydroquinone such as 2-methylhydroquinone, or a compound having tri-alkyl substituents on hydroquinone such as 2,3,5-trimethylhydroquinone tends to have a deteriorated symmetry of the molecule, and is thus in a liquid or semisolid state at room temperature, which is not preferable for the purpose.

Further, an epoxy resin of a compound having alkyl at 2- and 6-positions of hydroquinone such as 2,6-di-tert-butylhydroquinone is considered to have a steric hindrance action to the epoxy group and thus tends to reduce the curing speed of the epoxy resin, having inferior molding productivity.

An alkyl substituent of $C_1$ tends to give an insufficient moisture resistance, and an alkyl substituent of $C_7$ or more tends to result in an increased melt viscosity and degradation of crystallinity. Therefore, the alkyl substituent is preferably $C_2$ to $C_6$, and tert-butyl and secbutyl are particularly preferable.

If the crystal melting point is lower than 50° C., some of the crystal tends to melt at room temperature, involving a handling problem. If the crystal melting point exceeds 150° C., a high molding temperature is required to achieve low viscosity, which is disadvantageous in view of the narrow processing temperature range.

Here, the crystal melting point means a peak top temperature of crystal melting peak measured by means of a differential scanning calorimeter (DSC) when the temperature is increased from room temperature at a rate of 10° C./min under a nitrogen flow.

When the melt viscosity is higher than 1 poise at 150° C., the composition filled with large amounts of inorganic fillers tends to have a problem in moldability or damage fine electronic devices, The melt viscosity used in the present invention is a value measured by an ICI cone and plate type viscometer at 150° C.

The epoxy resin of Formula [I] of the present invention is obtained by reacting 2,5-di-alkyl-substituted (alkyl being $C_2$ to $C_6$) hydroquinone with epichlorohydrin. This is achieved using a conventional method known in the art, and is not specifically limited.

Specifically, 2,5-di-alkyl-substituted (alkyl being $C_2$ to $C_6$) hydroquinone is mixed with epichlorohydrin in an amount of 1 to 20 moles based on hydroxyl group of the hydroquinone, and reacted in the presence of an alkali such as sodium hydroxide at 30° to 120° C. for 0.5 to 10 hours, or 2,5-di-alkyl-substituted (alkyl being $C_2$ to $C_6$) hydroquinone is mixed with epichlorohydrin in an amount of 1 to 20 moles based on hydroxyl group of the hydroquinone, and reacted in the presence of a quaternary ammonium salt such as tetraethylammoniumchloride at 30° to 150° C. for 0.5 to 10 hours to obtain polyhalohydrin, which is reacted at 30° to 120° C. for 0.5 to 10 hours in the presence of an alkali such as sodium hydroxide to obtain the epoxy resin. In the reaction, solvents such as alcohols, ketones, or non-proton polar solvents may be used as necessary.

Since the epoxy resin of 2,5-di-alkyl-substituted (alkyl being $C_2$ to $C_6$) hydroquinone obtained by the above reaction contains unreacted epichlorohydrin and alkali metal chloride, the unreacted epichlorohydrin is removed by evaporation from the reaction mixture, and the alkali metal chloride is removed by extraction with water, to obtain the objective epoxy resin.

In the present, invention, the epoxy resin of Formula [I] can be mixedly used with an appropriate amount of other epoxy resins. Blendable epoxy resins include, but are not limited to, bisphenol A type epoxy resin, bisphenol F type epoxy resin, tetrabromobisphenol A type epoxy resin, biphenyl type epoxy resin, phenol novolac type epoxy resin, o-cresol novolac type epoxy resin, brominated phenol novolac type epoxy resin, N,N,N,N,-tetraglycidyldiaminodiphenylmethane, and 1,1,2,2-tetrakis(glycidyloxyphenyl)ethane. These epoxy resins are mixed in a weight ratio of 100:0 to 10:90 with the epoxy resin of Formula [I] of the present invention.

The epoxy resin composition of the present invention can be cured with a conventional epoxy hardener. Usable epoxy hardeners include amines, acid anhydrides, aminopolyamide resin, polysulfide resin, phenol novolac resin, boron trifluoride amine complex, dicyandiamide, and the like.

Practical examples of the epoxy hardener include amines such as diethylenetriamine, triethylenetetramine, isphoronediamine, m-xylylenediamine, m-phenylenediamine, p-phenylenediamine, 4,4'-diaminodiphenylmethane, 4,4'-diaminodiphenylsulfone, 4,4'-diaminodiphenylether, and aniline-formaldehyde resin; acid anhydrides such as phthalic anhydride, hexahydrophthalic anhydride, nadic anhydride, methynadic anhydride, trimellitic anhydride pyromellitic anhydride, and benzophenonetetracarboxylic anhydride; aminopolyamide resin as a condensate of dimer acid and diethylenetriamine or triethylenetetramine; polysulfide resin having a mercaptan terminal group; borontrifluorideamine complex obtained from borontrifluoride and aniline, benzylamine, or ethylamine; novolac resin obtained by condensation of phenol, cresol, xylenol, or resorcinol with formaldehyde; and latent hardeners such as dicyandiamide, adipic acid dihydrazide, sebacic acid hydrazide, and the like.

Of these hardeners, for use as a sealing material, it is preferable to cure with a novolac resin, and phenol novolac resin is particularly preferable, and for use in laminate boards for printed circuits, dicyandiamide is often used.

In the novel epoxy resin composition of the present invention, these hardeners are used in such an amount that the active hydrogen in the hardener is 0.5 to 1.5 equivalent, preferably 0. 8 to 1.2 equivalent, based on 1 equivalent of the epoxy group in the epoxy resin constituents for amines, polyamide resin, polysulfide resin, borontrifluoride-amine complex, and novolac resin. For acid anhydrides, the hardener is used in such an amount that the acid anhydride in the hardener is 0.5 to 1.0 equivalent, preferably 0.7 to 0.9 equivalent, based on 1 equivalent of epoxy group in the epoxy resin constituents. For dicyandiamide, the hardener is preferably used in such an amount that the active hydrogen is 0.3 to 0.7 equivalent.

The novel epoxy resin composition of the present invention can be used in combination with an accelerator as necessary. Practical examples of the accelerator include tertiary amines such as triethylamine, tributylamine. dimethylbenzylamine, and diethylbenzylamine; quaternary ammonium salts such as benzyltrimethylammonium chloride and benzyltriethylammonium chloride; phosphines such as triethylphosphine and triphenylphosphine; phosphonium salts such as n-butyltriphenylphosphonium bromide; imidazoles such as 2- methylimidazole and 2-ethyl-4-methylimidazole; or organic acid salts thereof such as of acetic acid. Of these accelerators, imidazoles and phosphines are preferable.

The epoxy resin composition of the present invention can be cured with the above hardener, and as necessary, in combination with the accelerator. Or, alternatively, the epoxy resin composition can be dissolved in ketones such as acetone or methylethylketone; cyclic ethers such as dioxane or tetrahydrofuran: amides such as dimethylformamide or dimethylacetamide; or aromatic hydrocarbons such as benzene, toluene, or xylene, to which a hardener and, as necessary, an accelerator are added and evenly dispersed or dissolved, and then the solvent is removed to cure the composition.

Further, when the epoxy resin composition of the present invention is used as a sealing resin, the hardener, and the accelerator as necessary, is added, and in addition an inorganic filler such as silica powder, alumina, antimony trioxide, talc, or calcium carbonate; a release agent such as natural waxes, paraffins, or metal salts of straight-chain fatty acids; a fire-retardant agent such as chlorinated paraffin or hexabromobenzene; a coloring agent such as titanium white, carbon black, or iron red; a silane coupling agent, and the like may be appropriately added.

It is preferable that 100 parts of the epoxy resin composition of the present invention contains 26 to 5 parts by weight of he epoxy resin ingredient comprising the epoxy resin of Formula [I],14 to 2 equivalents of a hardener (including an accelerator), and 60 to 93 parts by weight of an inorganic filler.

Since the novel epoxy resin composition of the present invention is small in water absorption rate and low in stress, it is suitable for use in sealing materials and laminate materials for printed circuits. The present invention will now be described in detail with the Examples, but is not limited to the Examples.

DESCRIPTION OF REFERENCE EXAMPLE, EXAMPLES, AND COMPARATIVE EXAMPLES

Reference Example 1

Synthesis of 2,5-di-tert-butyl-hydroquinonediglycidylether

To 100 parts if 2,5-di-tert-butyl-hydroquinone, 500 parts of epichlorohydrin and 100 parts of diethyleneglycoldimethylether were added, and heated to 100° C. While the reaction mixture was maintained at 98° to 102° C., 72 parts of a 49 weight % aqueous sodium hydroxide solution was dropped in over 6 hours. During the dropping, epichlorohydrin was boiled as an azeotrope with water, and distilled water was removed out from he reaction system.

After completion of the reaction, epichlorohydrin was recovered under a condition of 5 mmHg at 160° C., and 330 parts of methylisobutylketone was added to dissolve the product. Then, 20 parts of a 10 weight % aqueous sodium hydroxide solution was added, reacted at a temperature of 80° to 90° C., 180 parts of hot water was added to dissolve the by-product salt, allowed to stand, and aqueous salt solution as the underlayer was removed out. After neutralization with an aqueous phosphoric acid solution, the resin solution was washed with hot water until the washed water is neutral, and the filtered. The resulting solution was heated to 160° under a reduced pressure of 5 mmHg to distill out methylisobutylketone to obtain 144 parts of the objective 2,5-di-tert-butyl-hydroquinonediglycidylether.

The product, when cooled, became a light yellow crystal, which lad an epoxy equivalent of 181 g/equivalent, a melting point of 135° C., a total chlorine content of 1200 ppm, and a melt viscosity at 150° C. of 0.1 poise or less. From the EEW of 181, n was approximately 0.1.

Examples 1–3, Comparative Examples 1–2

Evaluation as sealing material

The epoxy resin obtained in Reference Example 1, o-cresol novolac epoxy YDCN-702P (Tohto Kasei, epoxy equivalent: 203 g/equivalent, softening point: 75° C.), phenol novolac resin BRG-557 (Showa Highpolymer, hydroxy equivalent: 105 g/equivalent, softening point: 86° C.), brominated epoxy resin YDB-400 (Tohto Kasei, epoxy equivalent: 400 g/equivalent, bromine content: 49.3 wt %, softening point: 66° C.), triphenylphosphine (Kishida Kagaku, Extra Reagent, grade), fused silica (K. K. Tatsumori, Hulex RD-8), antimony trioxide (Nippon Seiko, ATOX-S), calcium stearate (Seido Kagaku), carbon black (Mitsubishi Kasei, MA-100), and silane coupling agent (Nippon Unicar, A-187) were mixed in ratios shown in the table below, kneaded at 140°–150° C. by a biaxial kneader SIKRC Kneader (Kurimoto Tekko), rapidly cooled and crushed to obtain molding materials. Using a metal mold, the molding compounds were precured by compression molding under conditions of 65 kg/cm$^2$, 120° C., 10 minutes. The precured molded materials were cured at 180° C. for 8 hours to prepare test specimens for, measuring physical properties. The results of physical property measurement are shown in Table 1. The physical properties were measured by the following methods.

(Glass transition temp. (Tg): Measured by a thermomechanical tester (TMA) Shimadzu TMC-30.

Flexural strength, flexural modulus: Measured according to JIS K6911.

Water absorption rate: A 50 mm diameter, 2 mm thick disk-formed molding was measured using a pressure cooker tester for a change in weight after 40 hours at 4.8 atm, 150° C., 100% RH.

As can be seen from Table 1, the epoxy resin composition according to the present invention, when used as a molding compound, is small in water absorption rate and low in flexural modulus (low stress).

TABLE 1

|  | Example | | | Comparative Example | |
|---|---|---|---|---|---|
|  | 1 | 2 | 3 | 1 | 2 |
|  | (Composition: in weight ratio) | | | | |
| Epoxy resin obtained in Reference Example 1 | 100 | 50 | 10 |  | 5 |
| o-Cresol novolac epoxy YDCN-702P |  | 50 | 90 | 100 | 95 |
| Phenol novolac resin BRG-557 | 58.0 | 54.9 | 52.4 | 51.7 | 52.0 |
| Brominated epoxy resin YDB-400 | 11.2 | 11.0 | 10.9 | 10.8 | 10.8 |
| Triphenylphosphine | 3.4 | 3.2 | 2.9 | 2.8 | 2.8 |
| Fused silica RD-8 | 1550 | 820 | 530 | 440 | 440 |
| Antimony trioxide ATOX-S | 11.2 | 11.0 | 10.9 | 10.8 | 10.8 |
| Calcium stearate | 5.2 | 3.0 | 2.3 | 2.2 | 2.2 |
| Carbon black MA-100 | 5.2 | 3.0 | 2.3 | 2.2 | 2.2 |
| Silane coupling agent A-187 | 6.6 | 3.8 | 2.9 | 2.7 | 2.7 |
| Curing condition | 65 kg/cm$^2$: 120° C. × 10 min. + 180° C. × 8 hrs. | | | | |
| Glass transition temp. (°C.) | 145 | 144 | 149 | 149 | 149 |
| Flexural strength 24° C. (kg/mm$^2$) 250° C. | 17.1 / 1.3 | 15.9 / 1.3 | 13.9 / 1.3 | 13.2 / 1.2 | 13.2 / 1.2 |
| Flexural modulus 24° C. (kg/mm$^2$) 250° C. | 1050 / 32 | 1170 / 40 | 1410 / 90 | 1540 / 134 | 1520 / 132 |

TABLE 1-continued

|  | Example | | | Comparative Example | |
|---|---|---|---|---|---|
|  | 1 | 2 | 3 | 1 | 2 |
|  | (Composition: in weight ratio) | | | | |
| Water absorption (%) | 0.78 | 0.81 | 0.88 | 0.99 | 0.96 |

What is claimed is:

1. An epoxy resin composition for encapsulating electronic parts comprising:

26 to 5 parts by weight of an epoxy resin component containing at least 5% by weight of an epoxy resin of the formula

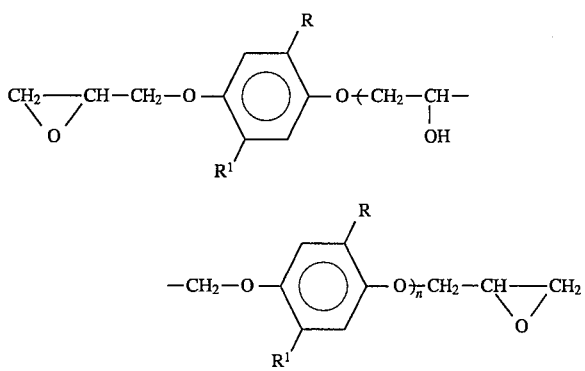

wherein

R and $R^1$ denote tert-butyl, and n has an average value of from 0 to 10, said epoxy resin of said formula having a crystalline melting point of 50° to 150° C. and a melt viscosity at 150° C. of 0.1 poise or less;

14 to 2 parts by weight of an epoxy hardener; and 60 to 93 parts by weight of an inorganic filler;

said epoxy resin composition totalling 100 parts by weight.

2. The epoxy resin composition of claim 1 wherein said epoxy resin component is a mixture of said epoxy resin of said formula with at least one selected from the group consisting of bisphenol A epoxy resin, bisphenol F epoxy resin, tetrabromobisphenol A epoxy resin, biphenyl epoxy resin, phenol novolac epoxy resin, o-cresol novolac epoxy resin, brominated phenol novolac epoxy resin, N,N,N'N'-tetraglycidyldiaminodiphenylmethane, and 1,1,2,2-tetrakis-(glycidyloxyphenyl)ethane.

3. The epoxy resin composition of claim 1 wherein said epoxy resin component is a mixture of said epoxy resin of said formula and brominated epoxy resin.

4. The epoxy resin composition of claim 1 wherein said epoxy resin component is a mixture of said epoxy resin of said formula, cresol novolac epoxy resin and brominated epoxy resin.

* * * * *